(12) United States Patent
Rozendal et al.

(10) Patent No.: US 7,439,047 B2
(45) Date of Patent: Oct. 21, 2008

(54) PROCESS FOR PRODUCING HYDROGEN

(75) Inventors: Rene Alexander Rozendal, HJ Hoorn (NL); Cees Jan Nico Buisman, RH Harich (NL)

(73) Assignee: Stichting Wet Sus Centre for Sustainable Water Technology, Leeuwarden (NL)

( * ) Notice: Subject to any disclaimer, the term of this patent is extended or adjusted under 35 U.S.C. 154(b) by 304 days.

(21) Appl. No.: 10/563,736

(22) PCT Filed: Jul. 9, 2004

(86) PCT No.: PCT/NL2004/000499

§ 371 (c)(1),
(2), (4) Date: Jun. 13, 2006

(87) PCT Pub. No.: WO2005/005981

PCT Pub. Date: Jan. 20, 2005

(65) Prior Publication Data

US 2007/0042480 A1      Feb. 22, 2007

(30) Foreign Application Priority Data

Jul. 10, 2003    (EP)    ................................. 03077183

(51) Int. Cl.
*C12P 3/00*     (2006.01)
*H01M 8/06*     (2006.01)

(52) U.S. Cl. ........................................... 435/168; 429/2
(58) Field of Classification Search ................. 435/168; 429/2
See application file for complete search history.

(56) References Cited

U.S. PATENT DOCUMENTS 7,354,743 B2 *   4/2008   Vlasenko et al. ............ 435/101

\* cited by examiner

*Primary Examiner*—Tekchand Saidha
(74) *Attorney, Agent, or Firm*—Medlen + Carroll, LLP

(57) ABSTRACT

A process for producing hydrogen from bio-oxidisable material is disclosed herein. The process comprises the steps of—introducing the bio-oxidisable material into a reactor provided with an anode and a cathode optionally separated by a cation exchange membrane and containing anodophilic bacteria in an aqueous medium;—applying a potential between the anode and cathode 0.05 and 1.5 volt, while maintaining a pH of between 3 and 9 in the aqueous medium;—collecting hydrogen gas at the cathode. The hydrogen production process can be intermittently switched to an electric power generation stage (biofuel cell) by adding oxygen to the cathode and separating the anode and cathode spaces by means of a cation exchange membrane.

9 Claims, 2 Drawing Sheets

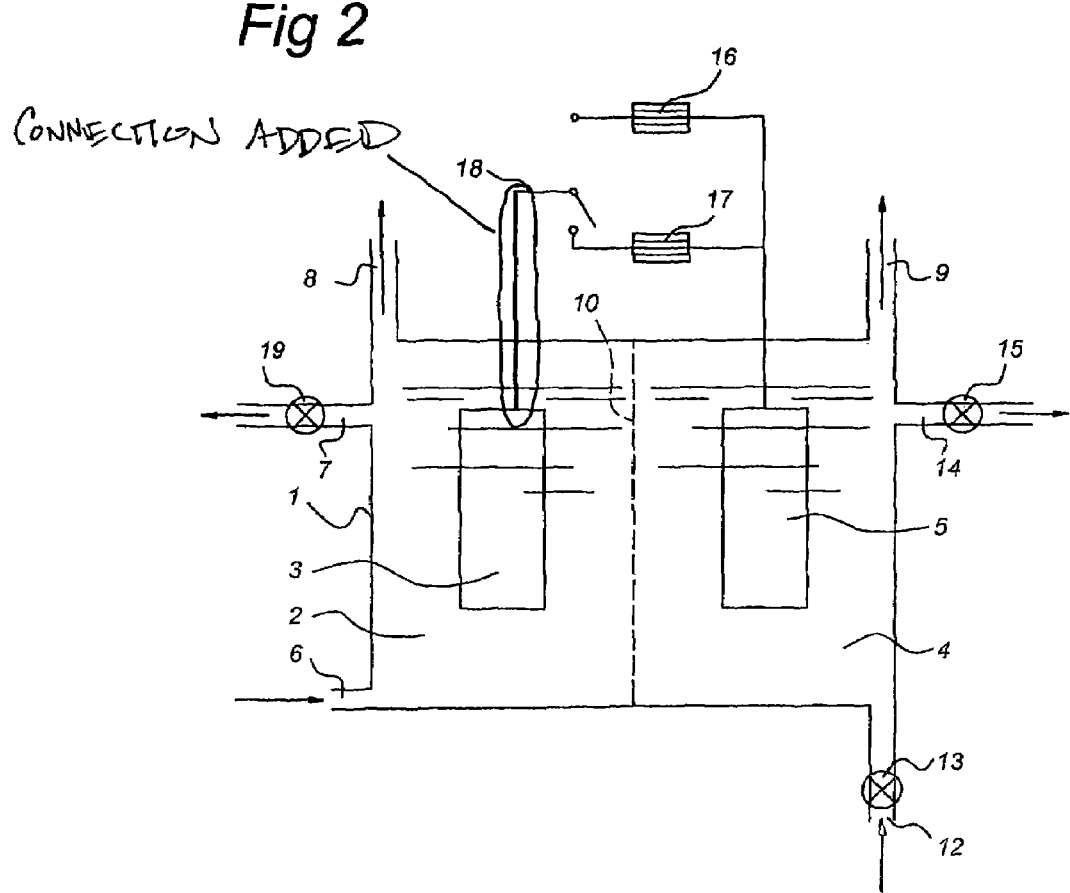

US 7,439,047 B2

1

PROCESS FOR PRODUCING HYDROGEN

Figure 1:
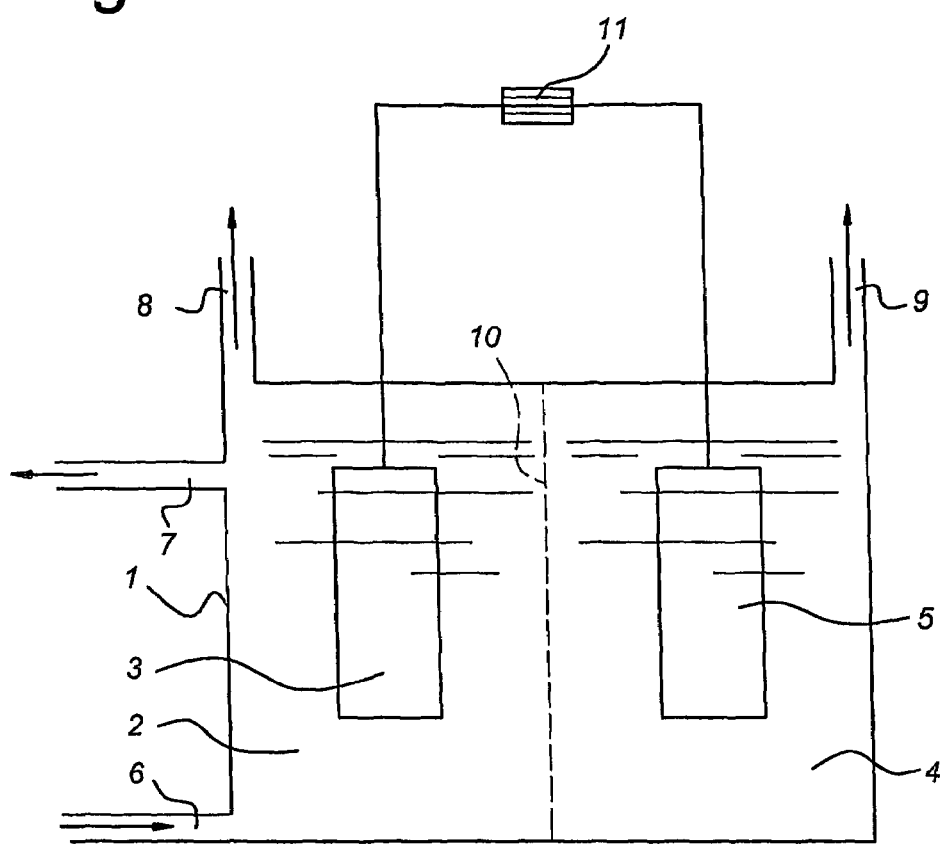

The present invention relates to a process for the biocatalysed production of hydrogen from bio-oxidisable material.

INTRODUCTION

This application is a U.S. national entry of International Application No. PCT/NL2004/000499, filed on Jul. 9, 2004, which claims priority to European Patent Application No. 03077183.6, filed on Jul. 10, 2003.

Expectations of the effects of global warming and the depletion of the fossil fuels have led to an enormous amount of research in the field of new energy carriers. These new energy carriers have to be renewable and preferably suitable as a transportation fuel. Many regard hydrogen gas as an ideal candidate for the future energy economy: the Hydrogen Economy. Hydrogen gas can be used in fuel cells, which can convert the hydrogen to electricity in a high yield (approx. 60%).

Conventional (chemical) methods for the production of hydrogen gas still rely on the conversion of non-renewable materials (e.g. natural gas). Examples of such methods are steam reforming (0.40 Nm$^3$ methane per Nm$^3$ H$_2$), methanol cracking (0.59 Nm$^3$ methane per Nm$^3$ H$_2$) and water electrolysis (1.3 Nm$^3$ methane per Nm$^3$ H$_2$) [Stoll R E, von Linde F, Hydrocarbon Processing, Dec. 2000:42-46].

A lot of research has been dedicated to the biological production of hydrogen gas from renewable sources, such as energy crops. Polysaccharides and ligno-celluloses from those energy crops can be hydrolysed to form hexoses and pentoses, which can be converted to hydrogen gas by fermentation subsequently. Glucose, for example, can be theoretically converted according to:

Glucose+6H$_2$O→12H$_2$+6CO$_2$    Reaction 1.

Only under favourable temperatures and hydrogen concentrations will this reaction yield enough energy for cell growth. It has been calculated that at a temperature of 60° C. a hydrogen pressure as low as 50 Pa is needed for reaction 1 to be favourable for cell growth [Lee M J, Zinder S H, Applied and Environmental Microbiology, 1988; 54:1457-1461]. Currently, there is no economically feasible method available of achieving such low hydrogen pressures. The conditions required are less extreme when part of the glucose is converted to fatty acids (e.g. acetic acid):

Glucose+2H$_2$O→4H$_2$+2CH$_3$COOH+2CO$_2$    Reaction 2.

But even then the hydrogen pressure has to be as low as 2,000-20,000 Pa (at 70° C.) in order to be favourable for cell growth [Groenestijn J W et al., International Journal of Hydrogen Energy, 2002;27:1141-1147] and only one third of the influent COD (=Chemical Oxygen Demand) is converted to hydrogen gas. The remaining two third of the COD is available as acetic acid and still needs to be converted to hydrogen gas to achieve 100% conversion. For this purpose a two stage process was developed. This biological process consists of a dark stage and a light stage. In the dark stage (hyper)-thermophilic microorganisms convert sugars to hydrogen gas and fatty acids according to reaction 2. As explained, it is critical to keep the hydrogen pressure below 2,000-20,000 Pa (at 70° C.) for the reaction to proceed. There are several methods to achieve this low hydrogen pressure, but all methods are energetically and/or economically costly.

2

Subsequently, the fatty acids are converted to hydrogen gas in the light stage by mesophilic photoheterotrophic bacteria. This conversion can be represented by reaction 3:

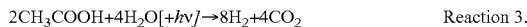
2CH$_3$COOH+4H$_2$O[+$h\nu$]→8H$_2$+4CO$_2$    Reaction 3.

The net total of reactions 2 and 3 equals reaction 1. However, a problem with this light stage, that still has to be overcome in order to get economically feasible conversion rates, is that the process is severely limited by the amount of sun hours during a day and the amount of (sun)light that can be introduced into the reactor; this would require reactors with excessively large surface areas. A further overall problem is that a hydrogen/CO$_2$ gas mixture is produced in both stages which needs to be separated to get a pure hydrogen gas stream.

Bioelectricity has been another approach to the development of a society based on sustainable energy. Some known (metal-reducing) microorganisms (e.g. Shewanella putrefaciens, Geobacter sulfurreducens, etc.) are able to use electrodes as electron acceptor. So, instead of using for example oxygen as a direct electron acceptor, the microorganisms donate their electrons directly to an electrode. These microorganisms are thus electrochemically active and such microorganisms are called anodophilic micro-organisms.

This principle allows for a biofuel cell process set-up: bio-oxidisable material (COD) is converted in the anodic compartment, while anodophilic bacteria transfer electrons to the anode. E.g. for glucose:

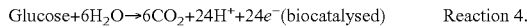
Glucose+6H$_2$O→6CO$_2$+24H$^+$+24$e^-$ (biocatalysed)    Reaction 4.

In the cathodic compartment electrons are transferred to oxygen from the cathode:

6O$_2$+24H$^+$+24$e^-$→12H$_2$O    Reaction 5.

The anode and the cathode are connected by an electrical circuit and the anodic and cathodic compartments are separated by a proton permeable membrane. Kim et al. showed that it was possible to generate electricity in such a biofuel cell using the metal-reducing bacterium Shewanella putrefaciens growing on lactate [Kim et al., Enzyme and Microbial Technology, 2002;30:145-152; see also WO 01/04061].

In an open circuit set-up a potential built up to 0.6 Volt was measured. Furthermore, cyclic voltammetry tests with bacterial suspensions showed that the potential in the fuel cell could even be as high as 0.8 Volt. However, when the electrical circuit was closed and a resistance of 1000Ω was put in, Kim et al. detected an electrical current of approx. 0.02-0.04 mA, implying a potential of only 0.02-0.04 Volt.

Theoretically, a voltage of approximately 1.15 Volt can be achieved in a fuel cell working on lactate (1.23 Volt on glucose) under the conditions described by Kim et al.,. but because the microorganisms take a part of this energy for maintenance and/or cell growth, this maximum will never be achieved in a biofuel cell. However, the yield that Kim et al. achieved in their process set-up (0.04 Volt/1.15 Volt=3.5%) is much lower than theoretically possible in this biofuel cell (0.8 Volt/1.15 Volt=70%), because in their process set-up, by providing oxygen as the electron acceptor, the anodophilic microorganisms are given the choice to release the electrons at any possible energy level above the energy level of the oxygen/water redox couple. The lower the energy level the electrons are released, the more energy the microorganisms gain for themselves for use in maintenance and cell growth. So, by using oxygen as the electron acceptor in a biofuel cell, a selection criterion is being created that selects for microorganisms that release the electrons at low energy levels. The microorganisms that do so, outcompete the microorganisms that release the electrons at a higher energy level, because they keep more of the energy for themselves and can thus grow faster. The more energy from the bio-oxidisable material the anodophilic microorganisms take for themselves, the more energy is lost for electricity production and thus low yields are achieved in the biofuel cell as described by Kim et al.

DESCRIPTION OF THE INVENTION

It was found that hydrogen can be produced in a bio-electrochemical process, by applying a potential between the anode and cathode of a bio-electrochemical cell that is necessary and sufficient for the electrons generated in the biochemical degradation of bio-oxidisable material to be transferred to protons and thus to generate molecular hydrogen.

Thus, the invention allows the ability of anodophilic bacteria to transfer electrons to an electrode to be used in a very effective and efficient process for the production of hydrogen gas from bio-oxidisable materials. In contrast to a biofuel cell, not oxygen, but hydrogen ions are used as the electron acceptor. At the anode, bio-oxidisable material is converted as in the biofuel cell. As an example, the following reaction applies to glucose:

$$\text{Glucose} + 6H_2O \rightarrow 6CO_2 + 24H^+ + 24e^- \text{(Biocatalysed)} \quad \text{Reaction 4.}$$

At the cathode, electrons are transferred to hydrogen ions instead of oxygen, so that hydrogen gas is produced:

$$24H^+ + 24e^- \rightarrow 12H_2(g) \quad \text{Reaction 6.}$$

As another example, the following reactions apply to hydrogen sulphide:

$$H_2S \rightarrow 2H^+ + S^0 + 2e^- \text{(Biocatalysed)} \quad \text{Reaction 7.}$$

$$2H^+ + 2e^- \rightarrow H_2(g) \quad \text{Reaction 6'.}$$

Under standard conditions, the Gibbs energy of the reaction for glucose is only slightly positive (approx. 3 kJ/mol glucose), meaning that energy is needed for this reaction to run and a voltage has to be applied (instead of produced by the microorganisms in a biofuel cell). In theory this would cost only approximately 0.01 Volt. However, because the microorganisms that catalyse this reaction also need energy for cell growth and maintenance, the voltage has to be higher. By applying the right voltage over the cell between 0 and 1.23 V, just enough energy is provided to the anodophilic microorganisms to perform their maintenance and cell growth processes, while the remainder of the energy of the bio-oxidisable material is recovered as hydrogen gas. In this way a selection criterion is created that selects for microorganisms that release the electrons at a high energy level, meaning that high yields can be achieved of hydrogen gas production from bio-oxidisable material.

It was found that applying a (single-cell) potential between 0.05 and 1.5 volt, preferably between 0.1 and 1.2 V, more preferably up to 0.7 V and especially between 0.2 and 0.5 volt, allows an efficient production of hydrogen gas, while maintaining a sufficient growth and maintenance of the bacterial population. For an acceptable bacterial viability, the pH in the bio-electrochemical reactor should preferably be moderately alkaline to moderately acidic, i.e. between 3 and 9, preferably between 4 and 8, especially from 5 to 7.

Thus, by applying the right conditions in this biocatalysed electrolysis process for the production of hydrogen gas, a selection criterion is created for the right microorganisms to grow. This makes sterilisation of the influent unnecessary.

The effective mixed culture of anodophilic micro-organisms able to oxidise every bio-oxidisable material will arise, when the right voltage is applied. This effective culture can be obtained by starting with activated sludge populations or anaerobic populations, of which a suitable variety is abundantly present in conventional (waste) water purification plants and biogas production plants, respectively. These populations are cultured under the conditions of the present process for a sufficient time for adaptation. Mesophilic populations, which are active at temperatures between e.g. 15 and 40° C. are preferred, but thermophilic bacteria can also be used, if desired. The process can also be started up with an inoculum of known anodophilic bacteria (e.g. Shewanella putrefaciens, Geobacter sulfurreducens, Rhodoferax ferrireducens etc.), with or without the start-up sludge cultures mentioned above.

Because the invention selects for micro-organisms that release the electrons at a high energy level, the anode will be covered with micro-organisms of such kind. When this anode/anodic compartment is temporarily connected to a cathode/cathodic compartment provided with oxygen as described by Kim et al., a high yield biofuel cell is created, s capable of converting bio-oxidisable material to electricity in a high yield. So besides being an efficient process for producing hydrogen gas from bio-oxidisable material, this invention also provides a way of selecting for anodophilic microorganisms, that release the electrons at a high energy level, and that can be temporarily used in a biofuel cell set-up as well. Because the selection criterion, as described earlier, is lost when switching to a biofuel cell mode, the anode will transform into a low yield anode in time. By switching back to the hydrogen production mode the high yield microorganisms are selected for again.

By switching between hydrogen production and biofuel cell mode efficiently, without losing too much of the high yield microorganisms in the biofuel cell mode, the invention also provides a very efficient way to produce electricity from bio-oxidisable materials. By converting the produced hydrogen to electricity using a normal hydrogen fuel cell, a process that only produces electricity in high yields, is achieved.

Accordingly, the electricity needed for the hydrogen production, to apply the voltage, can be obtained during the biofuel cell mode or by the conversion of part of the produced hydrogen to electricity in a normal fuel cell (approx. 60% yield). Overall COD yields as high as 60-85%, or even up to 100% can be obtained from COD conversion to hydrogen gas, which can compete with COD yields of conventional non-sustainable methods. While those methods are based on the conversion of valuable raw materials (e.g. natural gas (see above)), this invention can use every bio-oxidisable COD-containing (waste) stream as an influent and convert it to hydrogen gas efficiently (see table 1.). As used herein, COD yield refers to the electron yield, i.e. the percentage of electrons in the hydrogen produced vs. the electron input.

TABLE 1

COD yields of conventional (chemical) hydrogen production methods compared to hydrogen production by biocatalysed electrolysis of bio-oxidisable COD-containing (waste) streams.

| Hydrogen Production Method | COD Yield (%) | Raw Material |
|---|---|---|
| Biocatalysed Electrolysis | 60-100 | Bio-oxidisable COD-containing (waste) streams |
| Steam Reforming | 63 | Methane (Natural Gas) |

TABLE 1-continued

COD yields of conventional (chemical) hydrogen production
methods compared to hydrogen production by biocatalysed
electrolysis of bio-oxidisable COD-containing (waste) streams.

| Hydrogen Production Method | COD Yield (%) | Raw Material |
|---|---|---|
| Methanol Cracking | 45 | Methane (Natural Gas) |
| Water Electrolysis | 19 | Methane (Natural Gas) |

The present invention can function with and without a cation exchange membrane between the anodic and cathodic compartments in the hydrogen production mode, because a voltage is applied instead of generated by the microorganisms. Another advantage is that hydrogen (cathode) and carbon dioxide (anode) are produced separately from each other, in contrast with the two stage (hyper)thermophilic and mesophilic photoheterotrophic fermentation during which a hydrogen/carbon dioxide mixture is produced. Accordingly, no extra energy has to be put into the separation of the gases, and either or both of the gases can be collected as valuable materials. Optionally, as with conventional water electrolysis, the hydrogen can even be produced at elevated pressures at the cost of an extra over-potential. For every 10-fold increase of the hydrogen pressure, an extra 0.03 Volt is necessary.

Also, a one stage process is achieved, instead of two stage as with the conventional biological hydrogen production process. Further, this process set-up gets around the light problem in the light stage of conventional biological two stage process, because no light is needed. Lastly, the process is not limited to an input of sugars; practically every bio-oxidisable material can be used for the production of hydrogen with biocatalysed electrolysis.

The present process can be carried out in a reactor having the characteristics of an electrolysis cell. The reactor comprises an anodic compartment and a cathodic compartment, optionally separated by a cation-exchange membrane, a controllable DC power source to be connected to the anode and cathode, an inlet for (dissolved) bio-oxidisable material, a liquid effluent outlet, an outlet for carbon dioxide gas and an outlet for hydrogen gas, optionally with a hydrogen storage facility. In the bimodal variant, wherein hydrogen production is alternated with power generation, a suitable inlet for oxygen/air and a liquid outlet in the cathodic compartment are also provided.

The membrane is a non-electron-conducting cation-exchange membrane of a suitable, e.g. polymeric material as conventionally used in fuel cells (e.g. Nafion™). It can be used in the bimodal embodiment (hydrogen production alternated with power generation) for keeping oxygen separated from the anode space. In case of hydrogen production only, the membrane may be dispensed with, but for an optimal gas separation the presence of the membrane is preferred. Ideally, the electrodes are dimensioned such that the cell can process 10 kg of COD per $m^3$ of reactor volume per day (order of magnitude) at typical current densities of between 0.1 to 10 A per $m^2$ of anode surface area (order of magnitude). The electrodes can be made of a metal or graphite/carbon or of a conductive polymer, e.g. containing copper or another metal or carbon. The cathode can contain or consist of a catalytic material (such as platinum), so that hydrogen is produced efficiently at low over-potentials. The cathode can be placed in the aqueous medium (solution), or it can be a gas diffusion type electrode placed against the membrane and directly producing hydrogen in the gas phase. The anode compartment contains the anodophilic populations, which will grow on the anode surface. Thus, for example, the reactor can be set up as a fixed film reactor in which the anode is used as a carrier.

A schematic diagram of a reactor set-up for hydrogen production with biocatalysed electrolysis is given in FIG. 1. The reactor comprises a reactor cell 1, having an anode compartment 2 with anode 3, and a cathode compartment 4, with cathode 5. The anode has a liquid inlet 6 for bio-oxidisable material, a liquid outlet 7 and a carbon dioxide gas outlet 8. The cathode compartment has hydrogen gas outlet 9. The anode and cathode compartments are optionally separated by a membrane 10. The anode and cathode are connected to a DC power supply 11. The flow of (dissolved) bio-oxidisable material enters through 6 and, after the biocatalysed reaction at the anode, the effluent (now poor with respect to its bio-oxidisable material content) exits through 7. If an adequate potential is applied between the anode and the cathode, bio-oxidisable material is consumed at the anode, while hydrogen gas is produced at the cathode and collected from gas outlet 9. At the same time carbon dioxide gas is produced at the anode and collected from gas outlet 8. It should be stressed that the figure is only schematic and is neither indicative of dimensions, nor restrictive as to further parts or variations.

In the bimodal embodiment, the hydrogen production and power production modes can be activated by simple operation of the relevant valves and connectors, as described below. It is preferred that the power production mode is not operated continuously for more than 3 days, especially more than 24 hours, so as to avoid deterioration of the anodophilic population. Preferably the ratio of activation periods of the hydrogen production mode and the power generation mode is between 1:4 and 4:1, more preferably between 2:3 and 3:2. A very suitable regimen is a 24 hour cycle comprising 1 or 2 hydrogen production stages of 4-12 hours interrupted by DC power supply stages of 4-12 hours, for example. Hydrogen production (=power consumption) can advantageously take place at times of low general power consumption, especially at night, while the reverse applies to power generation.

A schematic diagram of a bimodal reactor according to the present invention is depicted in the accompanying FIG. 2. Similar parts of FIGS. 1 and 2 have the same reference number. The reactor comprises a reactor cell 1, having an anode compartment 2 with anode 3, and a cathode compartment 4, with cathode 5, and a liquid inlet 6 for bio-oxidisable material, liquid outlet 7 with valve 19 and a carbon dioxide gas outlet 8. The cathode compartment has a gas inlet 12 for oxygen (air) with a valve 13, a waste gas outlet 9 a liquid outlet 14 with a valve 15. The anode and cathode compartments are separated by a membrane 10. The anode and cathode are connected to a DC power supply 16 or a power-consuming device 17 with a switch 18 between 16 and 17. Again, the figure is only schematic and is neither indicative of dimensions, nor restrictive as to further parts or variations.

In the power production mode A, switch 18 is connected to the power consuming device 17. Valve 15 is closed and valves 13 and 19 are open. The flow of (dissolved) bio-oxidisable material enters through 6 and, after the biocatalysed reaction at the anode, the effluent (now poor with respect to its bio-oxidisable material content) exits through 7. The carbon dioxide that is produced due to the anode reaction is removed through gas outlet 8. Protons can enter the cathode compartment through membrane 10. Oxygen (e.g. from air) is fed to the cathode and reacts with the protons and the electrons from the cathode to form water; waste gas escapes through outlet 9. Excess water in the cathode, produced due to the cathode reaction, can be removed by opening valve 15.

In the hydrogen production mode B1, switch 18 is connected to the DC power supply 16. Valves 13 and 15 are closed and valve 19 is open. The flow of (dissolved) bio-oxidisable material enters through 6 and, after the biocatalysed reaction at the anode, the effluent (now poor with respect to its bio-oxidisable material content) exits through 7. The carbon dioxide that is produced due to the anode reaction is removed through gas outlet 8. Protons can enter the cathode compartment through membrane 10, where they react with the electrons from the cathode to form hydrogen gas. No additional gas is added to the cathode compartment. Hydrogen gas is collected from outlet 9, and can be stored in storage facility (not shown), or directly be used in a hydrogen consuming process (not shown).

In the membrane-less variation of the hydrogen production mode B2, membrane 10 is absent. However, to prevent intermixing of the gas phases of the anode and the cathode, a separator device (not shown) is placed in between both gas phases. Switch 18 is connected to the DC power supply 16. Valves 13 and 19 are closed and valve 15 is open. The flow of (dissolved) bio-oxidisable material enters through 6 and, after the biocatalysed reaction at the anode, the effluent (now poor with respect to its bio-oxidisable material content) exits through 14. The carbon dioxide that is produced due to the anode reaction is predominantly removed through gas outlet 9. Protons react with the electrons from the cathode to form hydrogen gas. No additional gas is added to the cathode compartment. Hydrogen gas is predominantly collected from outlet 9, and can be stored in a storage facility (not shown), or directly be used in a hydrogen consuming process (not shown).

The biocatalysed electrolysis process can be operated at autogenous temperature, i.e. without external temperature control, preferably between 15 and 40° C., more preferably between 25 and 39° C. The bio-oxidisable material can be any organic or inorganic material containing low-molecular-weight degradable or oxidisable compounds that can generally be treated in conventional aerobic or anaerobic biological reactors; examples include saccharides, fatty acids, proteins, alcohols, carbon monoxide, hydrogen sulphide, elemental sulphur, etc.

The appropriate population of anodophilic can be maintained by making use of the competition under the specific electron potential applied. Thus, by slight variation of the potential, the proper anodophiles having the desired electron-donating properties can outcompete the less efficient anodophiles.

The process described above for the production of hydrogen gas is also applicable with other than anodophilic organisms, such as *E. coli* by using electron mediators. An electron mediator is able to transport electrons from micro-organisms to an electrode surface by switching between its oxidised and reduced form. Examples of such electron mediators are known to the skilled person and comprise aromatic redox compounds, or dyes, such as benzyl viologen, methylene blue, neutral red and the like. Such electron mediators can be used at concentrations of 5-500 μmol per l. So instead of direct transfer of electrons from the micro-organisms to the electrode, an indirect transfer takes place via the electron mediator.

EXAMPLE 1

Biocatalysed Hydrogen Production

A reactor was operated under such conditions that biocatalysed electrolysis occurred and hydrogen evolution could be observed. The cell consisted of an anodic and a cathodic compartment separated by a proton exchange membrane (Nafion™). Both compartments had a liquid volume of 3.3 litres. The temperature of the system was controlled at 30° C. The anode consisted of a round graphite felt electrode (Fiber Materials, Inc., Scotland, diameter: 240 mm, thickness: 3 mm). The anode compartments was inoculated with effluent from a biological fuel cell containing anodophilic micro-organisms and was continuously fed (1.3 ml/min) with an aqueous solution containing 1 g/l of sodium acetate. During operation the pH in the anode was around 8.1. The anodic compartment was kept anaerobic by flushing it with nitrogen gas. The cathode was filled with 0.1 M phosphate buffer at a pH of 6.7. A right-angled piece of platinised platinum (dimensions: 20×5×0.2 mm) was used as cathode material. Prior to starting the experiments the cathodic compartment was flushed with nitrogen gas as to remove oxygen from the catholyte. When the current in the cell was kept at 2.5 mA using a potentiostat/galvanostat (μAutolab III, Ecochemie, The Netherlands), a voltage of 0.3 V was necessary to get hydrogen evolution at the cathode. The hydrogen evolution was found to be stoichiometric with the current flowing through the cell and lasted until the current was stopped.

The invention claimed is:

1. A process for producing hydrogen from bio-oxidisable material by:
    introducing the bio-oxidisable material into a reactor provided with an anode and a cathode and containing anodophilic bacteria in an aqueous medium;
    applying a potential between the anode and cathode of between 0.05 and 1.5 volt;
    collecting hydrogen gas from the cathode.

2. A process according to claim 1, in which the potential between the anode and cathode is between 0.2 and 0.7 volt.

3. A process according to claim 1, in which a pH of between 3 and 9, is maintained in the aqueous medium.

4. A process according to claim 1, in which the anodophilic bacteria are derived from activated sludge and/or anaerobic sludge.

5. A process according to claim 1, in which the anodophilic bacteria are replaced by or supplemented with non-anodophilic bacteria, and an electron mediator is present in the reactor.

6. A process according to claim 1, in which, in a stage subsequent to the hydrogen production stage, electric power is produced by interrupting the application of the potential and passing oxygen to the cathode.

7. A process according to claim 6, in which the duration of the hydrogen production stages and the power production stages have a ratio of between 1:4 and 4:1.

8. A process according to claim 1, in which pure carbon dioxide gas is collected at the anode.

9. A reactor suitable for carrying out the process according to claim 1, comprising a reactor cell containing an anode in an anodic compartment and a cathode in a cathodic compartment optionally separated by a proton-permeable membrane, a liquid inlet and one or two, optionally closable, liquid outlets, a gas inlet and optionally a second closable gas inlet, a gas outlet connected to the anodic compartment and a gas outlet connected to the cathodic compartment, a DC power supply and optionally a power consuming device.

* * * * *